United States Patent [19]

Hagelauer

[11] Patent Number: 4,955,143
[45] Date of Patent: Sep. 11, 1990

[54] APPARATUS AND METHOD FOR CONTROLLING AND ADJUSTING THE GEOMETRIC RELATIONSHIP BETWEEN ELECTRODE TIPS OF AN UNDERWATER SPARK DEVICE

[75] Inventor: Ulrich Hagelauer, Bottighofen, Switzerland

[73] Assignee: Storz Medical AG, Kreuzlingen, Switzerland

[21] Appl. No.: 340,796

[22] Filed: Apr. 20, 1989

[30] Foreign Application Priority Data

Feb. 10, 1989 [DE] Fed. Rep. of Germany ....... 3904049

[51] Int. Cl.$^5$ .............................................. G01B 3/30
[52] U.S. Cl. ......................................... 33/652; 33/645
[58] Field of Search ................. 33/652, 645, 644, 555; 445/67

[56] References Cited

U.S. PATENT DOCUMENTS 2,135,296 11/1938 Towne ................................... 33/652
2,498,823  2/1950 Peterson ............................... 33/652
2,656,615 10/1953 Rowell ................................. 33/652
2,896,334  7/1959 Dunderman ......................... 33/652
3,377,686  4/1968 Carpenter ............................. 29/203
3,805,393  4/1974 Lemelson ............................. 33/555
4,791,734 12/1988 Wojtkowiak ........................ 33/652

FOREIGN PATENT DOCUMENTS 3432942  3/1986 Fed. Rep. of Germany ........ 445/67

Primary Examiner—William A. Cuchlinski, Jr.
Assistant Examiner—D. Price
Attorney, Agent, or Firm—Evenson, Wands, Edwards, Lenahan & Mckeown

[57] ABSTRACT

A method and apparatus checks and adjusts the relative position of electrodes which form a so-called underwater spark gap device, particularly for medical purposes, and in which one electrode is fastened to the base part by means of at least one electrode holder. The method and apparatus employ an adjusting arrangement which positions the electrodes at a desired position with respect to axial displacement, angularity between the axes, and electrode spacing. By means of a relative movement of the adjustment arrangement, in a direction which is vertical with respect to an electrode axis, the electrode holder or holders are plastically deformed in such a manner that the electrodes, after the rebounding of the electrode holder or holders, are located at the desired position.

14 Claims, 2 Drawing Sheets

APPARATUS AND METHOD FOR CONTROLLING AND ADJUSTING THE GEOMETRIC RELATIONSHIP BETWEEN ELECTRODE TIPS OF AN UNDERWATER SPARK DEVICE

BACKGROUND AND SUMMARY OF THE INVENTION

The present invention relates to a method and apparatus for controlling and adjusting the relative positions of electrode tips of an underwater spark gap device for medical applications, and more particularly to a situation wherein at least one tip of the underwater spark gap device is mounted by at least one electrode holder to a base plate.

The above mentioned underwater spark gap devices are, for example, incorporated in extracorporeal lithotripters, i.e. an instrument for crushing a vesical calculus. By means of a high voltage discharge between the electrode tips, a fluid is spontaneously evaporated, forming a spherically shaped shock front. This shock front can then be focused by an ellipsoidal reflector at a focal point.

Usually one electrode tip of the underwater spark gap device is mounted to a base plate, while the opposite electrode tip is held by an electrode holder comprising a series of rods, forming a kind of cage, which is itself mounted on the above-mentioned base plate.

In technical realizations of these extracorporeal lithotripters, the underwater spark gap devices may include the capability of removable electrode tips (as shown in devices provided by Technomed) or have the capability of interchangeable wearing parts (as shown in devices provided by Dornier). In both cases, intensity, pressure rise time and the reproducibility of the shock wave front depend on the condition and geometry of the electrode tips. The relevant geometric parameters are the distance, the alignment and the angularity of the electrode tips of the electrodes.

The electrode tips have to be adjusted within very narrow tolerances, in order to gain a reproducable spark discharge. This requires an elevated effort during production and a resulting increase in cost. Furthermore, the electrode holder cage may be deformed by mechanical stress, caused by the high pressures of several thousand bar experienced during spark discharge. Another problem is the increase of distance between the electrode tips caused by burndown as a result of normal wear. All the factors lead to a maladjustment of the electrodes which may subsequently lead to malfunction.

These above-noted problems may cause severe risks in that lithotripters based on spark gaps are frequently used in the medical area. The decreased efficacy of improperly adjusted electrode tips results in the requirement of a higher number of shocks during treatment, and subsequently to a prolonging of the time required for treatment and anesthesia of the patient. In the worse case, the therapeutic point of focus of the spark gap device may be dislocated, which means that the zone of maximal pressure is dislocated from the desired treatment area into nearby organ regions. The risk of organ bleedings, which is usually observed following extracorporeal lithotripty, is thus increased, causing stress and pain to the patient. This improper adjustment of the electrode tips may cause peculiar risks, if the treatment areas are located close to vessels, as in the case of treatment of the ureteral area. Lesions of vessels may occur and result in acute risks to the patients' health.

Medical lithogripters currently in use do not allow for the control or adjustment of the geometry of the spark gap. Furthermore, the operator cannot readjust the increased distance between the electrode tips caused by burndown. In order to lower the risks which result from the above-mentioned deficiencies, there is no alternative but to change the complete underwater spark gap assembly, even when this assembly has not been completely worn out, thus causing additional costs per treatment.

Therefore, it is an object of the present invention to provide a method for controlling and readjusting the relative positions of electrodes, forming a so-called underwater spark gap especially for medical applications, at least one electrode being mounted by an electrode holder to a base plate.

A further object of the present invention is to provide an apparatus for carrying out the method for performing the control and readjustment of the geometric parameters of underwater spark gaps.

Thus, certain advantageous embodiments of the present invention readjust the relative position of the electrode tips by a grooved adjustment tool which adapts to the configuration of the electrode holder to position the tips of the electrodes at a nominal position for proper alignment, angularity and electrode distance. By means of a relative movement within the adjustment tool, rods of the electrode holder cage are plastically deformed in such a way that the electrode tip carried by the electrode holder cage is positioned at its nominal position after this procedure.

One particular advantage of the present invention is that if the geometry of the adjustment tool and the freedom of the relative movement within the tool are suitably chosen, the nominal position of the electrode tips can be readjusted by a user without mechanical skills.

The method described with respect to preferred embodiments of the invention also provides the further advantage that it can also be used during the manufacture of underwater spark gaps to simplify the adjustment of the electrode tips during the production procedure and thereby reduce associated production costs.

According to one particular embodiment of the present invention, a mechanical adjustment of the relative position of the electrode tips is performed by an axially symmetrical bending of one or more rods forming the electrode holder cage to thereby achieve the desired adjustment of the alignment, angularity and electrode distance of the electrode tips in a single step.

According to another embodiment of the present invention, the electrode distance can be readjusted independently from alignment and angularity adjustments. This can, for example, be achieved by changing the relative distance between the movable upper and lower segments of the adjustment tool.

Thus, in accordance with certain advantageous embodiments of the apparatus of the present invention, the apparatus includes a dividable adjustment tool for embracing the electrode holder cage of the spark gap device, the adjustment tool being shaped according to the outer contour of the electrode holder cage to position the electrode holder cage to a nominal position at which the tips of the electrodes are properly positioned with respect to alignment, angularity and electrode distance. To perform the adjustment, the adjustment tool for the electrode holder cage is rotated around an electrode axis relative to the holder at the base plate.

In accordance with a further embodiment of the present invention, the dividable adjustment tool comprises a pair of holders, one of the holders being fixed, while the opposite holder is rotated. The fixed holder attaches to the base plate of the spark gap device, while the electrode held by the electrode holder cage is inserted at the rotatable adapter. This arrangement permits a bending of the electrode holder cage to provide a precise readjustment of geometric relationship of the electrode tips.

Preferably, the adjustment tool is rotated around an electrode axis, as this results in a symmetrical bending of all the rods forming the electrode holder cage.

According to additional advantageous embodiments of the present invention, the rods of the electrode cage are only bent in a certain region, namely a region within the adjustment tool in which the rods are not inserted or embraced by the adjustment tool.

The adjustment tool provides the further advantage that it is not only suited to adjust the electrode tips, but also to control their relative positions. Thus, the adjustment tool provides the further feature that it may also be used as gauge to control the position of the electrode tips.

This control can be performed by adding an optical system according to one embodiment of the present invention which allows for the control of the position of the electrode tips visually or by means of an image processing system. Especially by using an image processing system, the method of controlling and adjusting the position of the electrode tips may be performed with an automated system. For example, a servo driven motor may be used to control the movements of the pair of movable holders of the adjustment tool relative to each other.

The control of the position of the electrode tips can also be performed by adding electrical contacts to the adjustment tool embracing the electrode tips, which close an electric circuit to generate a signal at the moment that the electrode tips are in contact with each other. This signal can be processed by an electrical control unit, for example a microprocessor controlled unit, which controls the relative movement of the movable holders of the adjustment tool according to the generated electrical signal mentioned above.

Other objects, advantages and novel features of the present invention will become apparent from the following detailed description of the invention when considered in conjunction with the accompanying drawings.

BRIEF DESCRIPTION OF THE DRAWINGS

FIGS. 1a and 2b illustrate the mounting arrangement of typical electrodes of an underwater spark gap device.

DETAILED DESCRIPTION OF THE DRAWINGS

Figure 1:
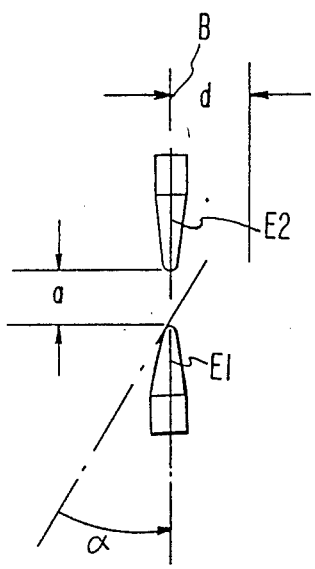
FIG. 1 illustrates the relevant geometric parameters for the nominal adjustment of electrodes forming an underwater spark gap.

FIG. 1 shows the relevant geometric parameters defining the relative position of two electrode tips E1 and E2 forming an underwater spark gap, namely the angularity "$\alpha$", the distance "a" between both electrode tips E1 and E2 and the degree of alignment "d" of the electrodes which have an electrode axis B extending between the two electrodes.

Figure 2A:
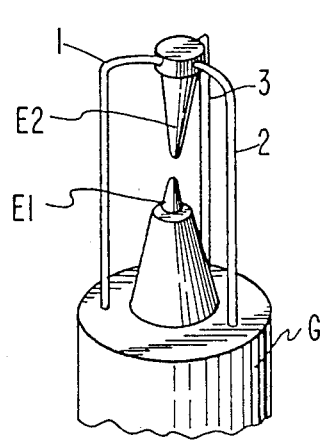

FIG. 2a shows the typical suspension arrangement of both opposite electrode tips E1 and E2. The electrode E2 is held by an electrode holder having rods 1, 2, 3 forming a kind of cage which allows a non-attenuated propagation of the spherical shock wave. The rods 1, 2, 3 are mounted to the base plate G.

As mentioned above, for a plurality of reasons, such as manufacturing defects, the high mechanical stress experienced during sparking or the consumption of the electrodes due to ordinary wear, a deviation of the position of the electrode tips from their desired position may occur.

Thus, according to preferred embodiments of the invention, the adjustment of the electrodes takes place by a relative movement of the electrode holder in a direction which is vertical with respect to the electrode axis B extending between the electrode, the rods 1 to 3 being plastically deformed in such a manner that the electrodes, after the rebounding of the electrode holder or holders, are located in their desired, nominal position.

Figure 3:
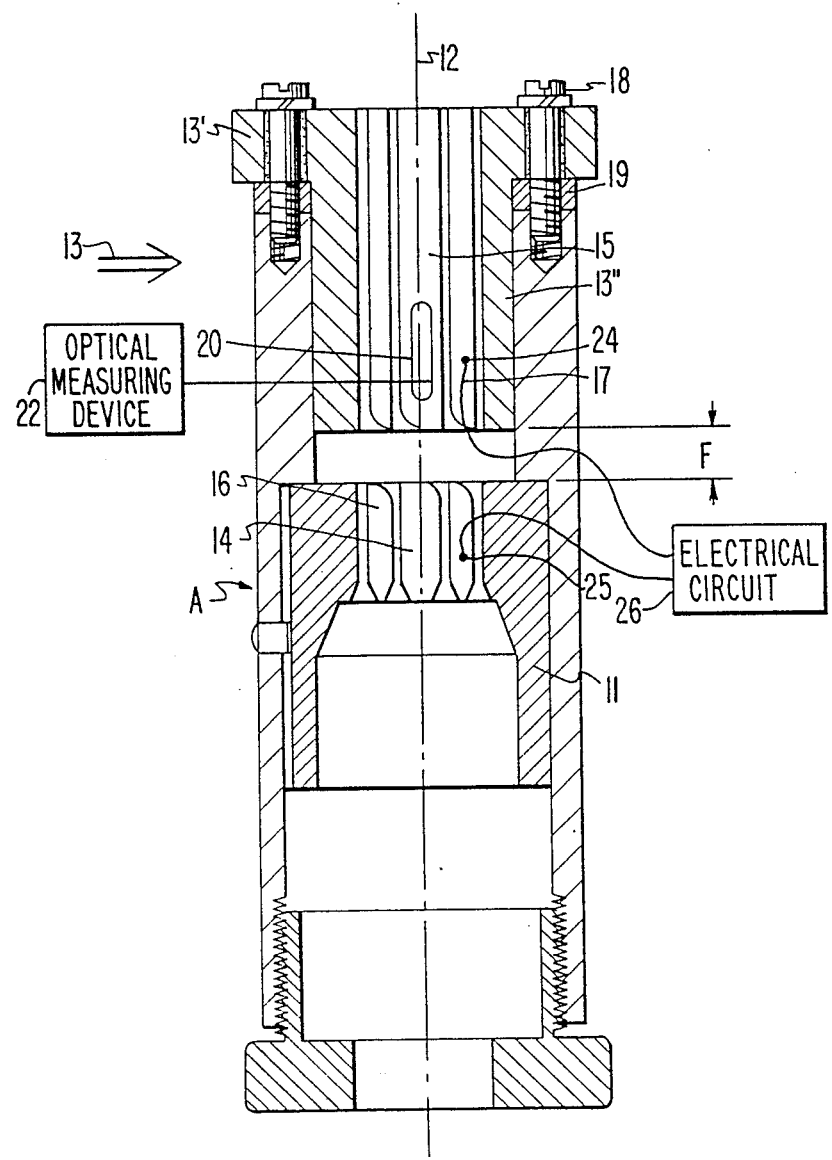
FIG. 3 illustrates an adjustment tool as described in accordance with one embodiment for carrying out the method of the present invention.

For this purpose, an adjustment tool A is used which is shown in FIG. 3. This adjustment tool has a stationary bending tool 11 and a bending tool 13 which can be rotated around an axis 12 with respect to the stationary bending tool 11, the axis 12 corresponding to aforementioned electrode axis B. The bending tools 11, 13 have receiving devices 14 and 15 for the electrodes E1 or E2 and receiving devices for engaging the cage rods 1, 2, 3 of which, in FIG. 3, only receiving devices 16 and 17 are shown. In addition, the adjustment tool A can be separated so that it can be placed against the electrodes E1 and E2 as well as the rods 1 to 3 and can also be removed therefrom.

Furthermore, the rotatable bending tool 13 includes two parts 13' and 13'' which are fastened together by means of fasteners such as screws 18 or the like. Thus, it is possible, by means of the insertion of spacers 19, to adjust the open distance F between the receiving devices 14, 15. The reason for this will be explained more fully below.

In addition, the adjustment tool A has at least one window 20 which permits a checking of the adjusting result.

The method of operation of a preferred embodiment of the adjustment tool A will be described below.

Figure 2B:
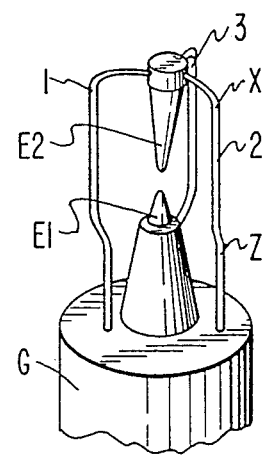

The adjusting principle of preferred embodiments of the present invention is based on a plastic deformation of the electrode holders 1 to 3 in the form of an axial, symmetrical bending of an upper part X of the electrode holder with respect to the lower part Z of the electrode holder as shown in FIG. 2b. Irrespective of an already existing asymmetrical deformation, the resulting plastic deformation of the electrode holder causes only an earlier or later start of the bending of the individual rods 1 to 3. After the deformation, the electrode holder has the required shape in order to keep errors of alignment and axis displacement within narrow limits. By means of a corresponding dimensioning of the clearance F, it is achieved that the elastic rebounding of the rods 1 to 3 of the electrode holder corresponds precisely to the desired distance measurement a to be adjusted.

As previously noted, another advantage of preferred embodiments of the invention is that all three mentioned geometrical parameters can be adjusted in one operation.

This results in a universal usefulness of the adjustment tool (a) as an adjusting arrangement in the manufacturing of underwater spark gaps, particularly for the elimination of errors of alignment and axis displacement, and (b) for the readjusting of the electrode spacing.

The adjusting may take place optically or automatically by means of a detected measuring deviation.

The measuring deviation, in this case, may be detected by means of an optical measuring device 22 which determines the position of the electrode tips with respect to one another. The checking may take place visually, for example, by means for a measuring microscope or by means of a camera with a connected image processing unit. For this purpose, the bending arrangement has the optical windows 20 in order to be able to check the electrode position before and after the adjusting by means of the measuring microscope or by the electronic image processing unit.

A checking of the measuring deviation may also be carried out by means of suitable electrical contact elements 24, 25 in the receiving devices 16, 17 for the electrodes which are connected to an electrical circuit 26 for controlling the positioning of the adjustment tool A in accordance with signals generated by the contacts 24, 25.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed is:

1. A method for controlling and adjusting the relative position of electrodes of a spark gap device, one electrode being mounted by at least one electrode holder to a base plate, the method comprising the steps of:
   engaging the at least one electrode holder; and
   positioning the at least one electrode holder about an electrode axis extending between the electrodes to a nominal position at which the electrodes are properly positioned with respect to at least one of an alignment, angularity and electrode distance of tips of the electrodes, the positioning step being accomplished by bending of the at least one electrode holder.

2. A method according to claim 1, wherein the bending step is accomplished by an orthogonal bending of the at least one electrode holder with respect tot he electrode axis.

3. A method according to claim 1, further comprising the step of adjusting the electrode distance independently of the alignment and angularity of the tips of the electrodes.

4. A method according to claim 1, wherein the spark gap device is an underwater spark gap device adapted for medical applications.

5. An apparatus for controlling and adjusting the relative position of electrodes of a spark gap device, one electrode being mounted by at least one electrode holder to a base plate comprising:
   electrode holder engaging means for engaging the at least one electrode holder; and
   electrode holder positioning means for positioning the at least one electrode holder about an electrode axis extending between the electrodes to a nominal position at which the electrodes are properly positioned with respect to at least one of an alignment, angularity and electrode distance of tips of the electrode;
   wherein the electrode holder engaging means comprises first and second electrode holder engaging means which are spaced a distance apart from one another and are adapted to engage an outer contour of the electrode holder; and
   wherein the electrode holder positioning means comprises bending means for bending the at least one electrode holder to assume the nominal position.

6. An apparatus according to claim 5, wherein one of the first and second electrode holder engaging means is fixed relative to the other.

7. An apparatus according to claim 6, wherein the first and second electrode holder engaging means are rotatable relative to one another about the electrode axis.

8. An apparatus according to claim 7, wherein the distance between the first and second electrode holder engaging means is varied by spacer means to set a desired electrode distance between the tips of the electrodes.

9. An apparatus according to claim 5, wherein the electrode holder engagement means has grooves for engaging rods of the electrode holder.

10. An apparatus according to claim 5, further comprising gauging means for controlling the distance between tips of the electrodes.

11. An apparatus for controlling and adjusting the relative position of electrodes of a spark gap device, one electrode being mounted by at least one electrode holder to a base plate comprising:
    electrode holder engaging means for engaging the at least one electrode holder; and
    electrode holder positioning means for positioning the at least one electrode holder about an electrode axis extending between he electrodes to a nominal position at which the electrodes are properly positioned with respect to at least one of an alignment, angularity and electrode distance of tips of the electrode; and
    optical means for generating signals which control the distance between tips of the electrodes by electrical or electronic processing.

12. An apparatus according to claim 11, further comprising control means for automatically controlling the electrode holder positioning means in accordance with the signals generated by the optical means.

13. An apparatus for controlling and adjusting the relative position of electrodes of a spark gap device, one electrode being mounted to at least one electrode holder to a base plate comprising:
    electrode holder engaging means for engaging the at least one electrode holder; and
    electrode holder positioning means for positioning the at least one electrode holder about an electrode axis extending between the electrodes to a nominal position at whidch the electrodes are properly positioned with respect to at least one of an alignment, angularity and electrode distance of tips of the electrode;
    electrical contact means for generating a signal condition activating an electrical circuit means for indicating a nominal positioning of the electrode tips;
    and further conprising control means for automatically controlling the electrode holder positioning means in accordance with the signal condition generated by the electrical contact means.

14. An apparatus according to claim 5, further comprising electrode engaging means for engaging the electrodes of the spark gap device.

* * * * *